United States Patent [19]

Kneuper et al.

[11] Patent Number: 5,696,297
[45] Date of Patent: Dec. 9, 1997

[54] PREPARATION OF ALDEHYDES

[75] Inventors: Heinz-Josef Kneuper, Mannheim; Rocco Paciello, Dürkheim; Michael Röper, Wachenheim, all of Germany

[73] Assignee: BASF Aktiengesellschaft, Ludwigshafen, Germany

[21] Appl. No.: 510,540

[22] Filed: Aug. 2, 1995

[30] Foreign Application Priority Data

Aug. 3, 1994 [DE] Germany ............... 44 27 428.9

[51] Int. Cl.$^6$ ............................................. C07C 45/50
[52] U.S. Cl. .................... 568/454; 568/451; 568/455
[58] Field of Search ........................ 568/451, 454, 568/455

[56] References Cited

U.S. PATENT DOCUMENTS

| | | | |
|---|---|---|---|
| 3,984,478 | 10/1976 | Homeier . | |
| 4,148,830 | 4/1979 | Pruett et al. . | |
| 4,400,547 | 8/1983 | Dawes et al. | 568/454 |
| 4,504,588 | 3/1985 | Gärtner et al. . | |
| 4,528,403 | 7/1985 | Tano et al. . | |
| 4,616,096 | 10/1986 | Cornis et al. . | |
| 4,731,485 | 3/1988 | Cornils et al. . | |
| 4,795,727 | 1/1989 | Bach et al. | 502/161 |
| 4,808,757 | 2/1989 | Cornils et al. . | |
| 5,091,350 | 2/1992 | Cornils et al. . | |
| 5,290,743 | 3/1994 | Chang et al. | 502/30 |
| 5,387,719 | 2/1995 | Kneuper et al. | 568/455 |

FOREIGN PATENT DOCUMENTS

| | | |
|---|---|---|
| 2080746 | 4/1993 | Canada . |
| 147 824 | 12/1984 | European Pat. Off. . |
| 173 219 | 3/1986 | European Pat. Off. . |
| 226 988 | 7/1987 | European Pat. Off. . |
| 26 04 545 | 8/1977 | Germany . |
| 32 35 029 | 3/1984 | Germany . |
| 33 38 340 | 5/1984 | Germany . |
| 33 47 406 | 7/1985 | Germany . |
| 34 11 034 | 9/1985 | Germany . |
| 34 12 335 | 10/1985 | Germany . |
| 41 35 050 | 4/1993 | Germany . |
| 1 565 716 | 4/1980 | United Kingdom . |
| WO 82/03856 | 11/1982 | WIPO . |

OTHER PUBLICATIONS

Kogyo Kagaku Zasshi, 72 (1969), 671.
Fette, Seifen, Anstrichmittel 76 (1974) 443.
Kohlpaintner, Dissertation (Phd Thesis), 123–139, Munich 1992.
Hermann et al., Angew. Chem. 105 (1993) 1588 et seq.
Abatjoglou et al. ACS Symp. Ser. 486 (1992) 229.
Organometallics 3, (1984) 932.
New Syntheses with Carbon Monoxide, Ed. Falbe, 38 et seq. 1980.
Chem. Ber. 1–2 (1969), 2238.
Tetrahedron Lett. 29 (1968), 3261.
Hydrocarbon Process, 54, Jun. issue (1975), 85–86.
Jamerson et al., J. Organomet. Chem. 193 (1980) C43.
Jamerson et al., J. Organomet. Chem. 192 (1980) C49.

*Primary Examiner*—C. Warren Ivy
*Assistant Examiner*—Sreeni Padmanabhan
*Attorney, Agent, or Firm*—Keil & Weinkauf

[57] ABSTRACT

Aldehydes or aldehydes and alcohols are prepared by hydroformylation of olefins of more than 3 carbon atoms by a process comprising the stage of hydroformylation by means of a rhodium catalyst homogeneously dissolved in the reaction medium, the separation of the rhodium catalyst from the discharge from the hydroformylation reaction and the recycling of the rhodium separated from the hydroformylation discharge to the hydroformylation stage, wherein the rhodium catalyst is extracted from the hydroformylation discharge into the aqueous phase by means of an aqueous solution of a water-soluble, phosphorus-containing complexing agent selected from the group consisting of the mono- or polysulfonated mono- and oligophosphines and/or from the group consisting of the mono- or polycarboxylated mono- or oligophosphines or the mono- or polysulfonated oligophosphites and the aldehyde or the aldehyde and the alcohol are isolated from the extracted hydroformylation discharge, the aqueous rhodium-containing extract is fed to a precarbonylation stage and is subjected to a precarbonylation in the precarbonylation stage in the presence of an essentially water-insoluble, organic liquid and in the presence of carbon monoxide or of a carbon monoxide-containing gas mixture.

23 Claims, No Drawings

PREPARATION OF ALDEHYDES

The present invention relates to a process for the preparation of aldehydes or aldehydes and alcohols by the hydroformylation of olefins of more than 3 carbon atoms, comprising the stage of hydroformylation by means of a rhodium catalyst homogeneously dissolved in the reaction medium, separation of the rhodium catalyst from the discharge of the hydroformylation reaction and recycling of the rhodium separated from the hydroformylation discharge into the hydroformylation stage.

The hydroformylation of olefins with carbon monoxide and hydrogen in the presence of transition metal catalysts is known. While α-olefins can be very readily hydroformylated using rhodium-containing, phosphine-modified catalysts (cf. J. Falbe, Ed.: New Syntheses With Carbon Monoxide, Springer, Berlin 1980, page 55 et seq.), this catalyst system is not very suitable for internal olefins and internal branched olefins nor for olefins with more than 7 carbon atoms (cf. Falbe, page 95 et seq.). Thus, internal carbon-carbon double bonds are hydroformylated only very slowly in the presence of such a catalyst. Since the hydroformylation product is as a rule separated by distillation from the catalyst dissolved homogeneously in the reaction system and the boiling point of the aldehyde formed in the hydroformylation increases with increasing number of carbon atoms and chain length to temperatures at which the rhodium-containing catalyst decomposes, this hydroformylation method is uneconomical for the hydroformylation of olefins of more than 7 carbon atoms. In the hydroformylation of polymeric olefins, for example of polyisobutene, the catalyst containing a noble metal cannot be recovered in reusable form.

On the other hand, in addition to α-olefins, internal olefins and internal branched olefins can also advantageously be hydroformylated using bare rhodium, ie. rhodium compounds which are dissolved homogeneously in the hydroformylation medium and are not modified with phosphorus-containing ligands, such as phosphines or phosphites. Such rhodium catalysts which have not been modified with phosphines or phosphites and their usefulness as a catalyst for the hydroformylation of the abovementioned classes of olefins are known (cf. Falbe, page 38 et seq.). The terms bare rhodium or bare rhodium catalysts are used in this application for rhodium hydroformylation catalysts which, in contrast to conventional rhodium hydroformylation catalysts, are not modified with ligands, particularly phosphorus-containing ligands, such as phosphine or phosphite ligands, under the hydroformylation conditions. Carbonyl or hydrido ligands are not understood as meaning ligands in this sense. It is assumed in the technical literature (cf. Falbe, page 38 et seq.) that the rhodium compound $HRh(CO)_4$ is the catalytically active rhodium species in the hydroformylation with bare rhodium catalysts, although this has not been definitively proven owing to the many chemical mechanisms taking place side by side in the hydroformylation reaction zone. Merely for the sake of simplicity, we make use of this assumption in this application too, without intending to restrict the scope of protection of the present application if at some time in the future a rhodium species other than the stated one should prove to be the actual catalytically active species. The bare rhodium catalysts form under the conditions of the hydroformylation reaction from rhodium compounds, for example rhodium salts, such as rhodium(III) chloride, rhodium(III) nitrate, rhodium(III) acetate, rhodium(II) acetate, rhodium(III) sulfate or rhodium (III) ammonium chloride, from rhodium chalkogenides, such as rhodium(III) oxide or rhodium(III) sulfide, from salts of oxo acids of rhodium, for example the rhodates, from rhodium carbonyl compounds, such as $Rh_4(CO)_{12}$ and $Rh_6(CO)_{16}$, or from organo rhodium compounds, such as acetonylacetonatorhodium dicarbonyl or cyclooctadienerhodium acetate or chloride, in the presence of $CO/H_2$ mixtures, which are usually referred to as synthesis gas. For carrying out hydroformylations with bare rhodium, reference may be made here, for example, to the following publications: U.S. Pat. No. 4,400,547, DE-A 33 38 340, DE-A 26 04 545, WO 82/03856, Chem. Ber. 102 (1969), 2238, Tetrahedron Lett. 29 (1968), 3261 and Hydrocarbon Process. 54, June issue (1975), 85–86.

However, hydroformylation with bare rhodium also has the disadvantage that, owing to the thermal load during the working up of the hydroformylation product by distillation, the thermally unstable rhodium catalyst (cf. U.S. Pat. No. 4,400,547) undergoes partial decomposition to metallic rhodium, which is deposited on the walls of the reactor and of the pipelines. The deposited rhodium metal cannot be recycled to the hydroformylation reaction since it cannot be converted into the catalytically active rhodium compound under the hydroformylation conditions. The rhodium losses resulting from this chemical behavior of bare rhodium catalysts have to date prevented large-scale industrial use of this process.

DE-A 33 38 340 and U.S. Pat. No. 4,400,547 describe processes for hydroformylation by means of bare rhodium catalysts, in which, in order to prevent the deposition of rhodium, a phosphine or phosphite is added to the discharged reaction mixture from the hydroformylation which, by the formation of phosphine and/or phosphite complexes, protect the rhodium catalyst from thermal decomposition in the course of working up the discharged hydroformylation mixture by distillation. After the end of the distillation, the rhodium-containing bottom product from the distillation is treated with an oxidizing agent, rhodium being liberated in catalytically active form from the relevant phosphine or phosphite complexes and the phosphine and phosphite ligands being oxidized to the corresponding phosphine oxides and phosphates which do not form rhodium complexes under hydroformylation conditions. The oxidized bottom product from the distillation is then used again as a catalyst for the hydroformylation. The oxidized phosphorus compounds formed in the oxidation generally do not interfere with the hydroformylation but, owing to the process, accumulate in this hydroformylation circulation, making it necessary constantly to remove a bleed stream of this catalyst solution from the hydroformylation circulation and to replace it with fresh catalyst solution. The catalyst solution removed must be subjected to a separate procedure for recovering the rhodium present therein.

WO 82/03856 relates to a process for rendering unmodified, ie. bare, rhodium catalysts heat-stable, in which process the discharge from the hydroformylation reaction is treated with an oxygen-containing gas, with the result that some of the aldehydes formed are oxidized to the corresponding carboxylic acids, which react with the rhodium catalyst in the working up by distillation and form heat-stable rhodium carboxylates, which can again be used as catalysts for the hydroformylation. The disadvantage of this process is the reduction in the yield as a result of the partial oxidation of the aldehydes produced to carboxylic acids. Moreover, this process is limited to hydroformylations in which distillable products are formed: for example, the rhodium catalyst cannot be separated from the hydroformylation product of the polyisobutene in this process.

In order to avoid rhodium losses, according to U.S. Pat. No. 3,984,478 a hydroformylation process was developed in which the hydroformylation is carried out in the presence of a phthalocyanine which may be sulfonated. Since some of the rhodium phthalocyanine complexes formed here are sparingly soluble or are soluble only in water but not in the organic hydroformylation medium, the hydroformylation is alternatively carried out in the presence of the solid rhodium phthalocyanines or in a two-phase system with water. However, the coordinate bond between the rhodium and the phthalocyanine in these complexes is very strong so that the rhodium remains bonded to the phthalocyanine even under the hydroformylation conditions. Consequently, the hydroformylation reaction takes place only at the hydroformylation medium/solid phthalocyanine interface or at the interface with the aqueous rhodium phthalocyanine complex solution, with the result that the reaction rate and hence also the space-time yield of the hydroformylation reaction are so low that this process cannot be operated economically.

DE-A 34 11 034 and DE-A 33 47 406 describe the separation of rhodium carbonyls and rhodium hydridocarbonyls, ie. bare rhodium, with the aid of water-soluble sulfonated or carboxylated phosphine ligands. The rhodium is extracted from the organic phase into the aqueous phase with the aid of these ligands and thus separated from the hydroformylation product which is soluble in the organic phase. In order to be capable of being used again as bare rhodium, the rhodium extracted in this manner and bonded to the phosphine ligands must be removed from the complex with this phosphine ligand by converting it, for example, into the salt of a higher carboxylic acid. This process has the disadvantage that it requires additional stages and starting materials (carboxylic acids) in order to convert the complexed rhodium into the relevant rhodium carboxylates. As an alternative, these publications propose using the phase consisting of the solvent water, rhodium and complexing agent directly as a catalyst system for the hydroformylation. However, this procedure, too, has considerable disadvantages: thus, the rhodium must be removed from these complexes under hydroformylation conditions and converted into bare rhodium. Apart from the fact that a considerable part of the hydroformylation reactor space is occupied by the aqueous phase containing the complex rhodium catalyst and can thus no longer be used for the hydroformylation, with the result that a larger reactor volume is required, which in turn leads to higher plant costs, degradation of the phosphine ligands takes place under the hydroformylation conditions used (cf. Jamerson et al., J. Organomet. Chem. 193, (1980), C43; Jamerson et al., J. Organomet. Chem. 192 (1980) C49; Abatjoglou et al., Organometallics 3, (1984) 932; Abatjoglou et al., ACS Symp. Ser. 486 (1992) 229; W. A. Herrmann et al: Angew. Chem. 105 (1993) 1588, in particular page 1600 et seq.). Since some of the degradation products of the phosphine ligand are highly effective catalyst poisons (cf. C. W. Kohlpaintner: thesis, Technische Universität München 1992, pages 123–139, in particular page 137), expensive regeneration steps must be taken in order to separate the rhodium and phosphine ligands from these degradation products, for example those as proposed in DE-A 32 35 029 and DE-A 41 35 050.

DE-A 34 12 335 relates to a process for hydroformylation with the aid of rhodium catalysts, in which the rhodium is complexed with a water-soluble sulfonated triphenylphosphine ligand. Under the reaction conditions stated, no bare rhodium is present. Accordingly, according to the examples, only 1-olefins but no internal olefins are hydroformylated.

Since long-chain olefins are virtually insoluble in the aqueous phase containing the complexed rhodium catalyst, a solubilizer must additionally be introduced into the reaction mixture since otherwise the productivity of the process is unsatisfactory. Instead of a solvent, EP-A 173 219 proposes the use of ultrasonics and EP-A 226 988 the use of a very high concentration (25–30% by weight) of the sulfonated arylphosphine ligand in the aqueous phase for solving this problem.

There has to date been no commercially satisfactory process for the direct preparation of internal, ie. branched aldehydes or isoaldehydes, by the hydroformylation of α-olefins, ie. olefins having a terminal double bond. Bott (Fette, Seifen, Anstrichmittel 76 (1974) 443) describes the synthesis of internal aldehydes from α-olefins by the isomerization thereof by means of cobalt octacarbonyl ($CO_2(CO)_8$) under a carbon monoxide atmosphere at 190° C. or over a sodium-on-alumina catalyst and subsequent hydroformylation of the internal olefins by means of homogeneous rhodium-triphenylphosphine catalysts. The disadvantage here is the use of two different catalysts for the individual reaction steps. Furthermore, internal olefins react with the rhodium triphenylphosphine catalyst too slowly for industrial purposes.

According to Fell et al. (Tetrahedron Lett. 29 (1968) 3261), 1-octene is isomerized at 100 bar carbon monoxide pressure and 190° C. over a catalyst which is prepared from $Rh_2O_3$ under 200 bar (1:1 $CO/H_2$) cold pressure and at 150° C. in hexane and which has been freed from hydrogen by repeatedly purging with carbon monoxide. The disadvantage of this process is the expensive catalyst preparation and the use of an inert solvent which occupies a considerable part of the available high-pressure reaction space and therefore reduces the space-time yield. Furthermore, Fell et al. did not solve the problem of the catalyst stability and catalyst regeneration. This process is therefore also uneconomical.

A study on the kinetics and mechanisms of the isomerization of α-olefins to internal olefins and the hydroformylation thereof is published in Kogyo Kagaku Zasshi, 72 (1969), 671.

It is an object of the present invention to provide a process for the preparation of aldehydes from long-chain and/or branched olefins with the aid of bare rhodium catalysts, by means of which, on the one hand, the problems of the separation of metallic rhodium in the working up of the hydroformylation products by distillation and the separation of the rhodium catalyst from non-distillable aldehyde products can be satisfactorily solved. For this purpose, it is intended to find a hydroformylation process in which complex ligands form coordinate bonds to the bare rhodium catalyst reversibly and as a function of the pressure of the carbon monoxide/hydrogen gas mixture, so that said catalyst is stabilized and can be extracted in working up by extraction. After the extraction, the complex rhodium catalyst is to be converted back into bare rhodium. It was intended in particular to ensure that no damage to the complex ligand occurs. Furthermore, it is intended to minimize rhodium losses in the course of the extraction and to find a combined hydroformylation/extraction process which permits the hydroformylation of internal olefins economically and with space-time yields, without having the disadvantages of the abovementioned processes.

It is a further object of the present invention to provide a process which permits the preparation of isoaldehydes from α-olefins in an economical manner. It is intended in particular to avoid the disadvantages of the prior art which are described above.

We have found that these objects are achieved by a process for the preparation of aldehydes or aldehydes and alcohols by the hydroformylation of olefins of more than 3 carbon atoms, comprising the stage of hydroformylation by means of a rhodium catalyst homogeneously dissolved in the reaction medium, separation of the rhodium catalyst from the discharge of the hydroformylation reaction and recycling of the rhodium separated from the hydroformylation discharge into the hydroformylation stage, wherein the rhodium catalyst is extracted from the hydroformylation discharge into the aqueous phase by means of an aqueous solution of a water-soluble, phosphorus-containing complexing agent selected from the group consisting of mono- or polysulfonated mono- and oligophosphines, from the group consisting of the mono- or polysulfonated oligophosphites and/or from the group consisting of the mono- or polycarboxylated mono- or oligophosphines, and isolating the aldehyde or the aldehyde and the alcohol from the extracted hydroformylation discharge, feeding the aqueous rhodium-containing extract to a precarbonylation stage and subjecting it to precarbonylation in the precarbonylation stage in the presence of an essentially water-insoluble, organic liquid and in the presence of carbon monoxide or of a carbon monoxide-containing gas mixture at from 5 to 600 bar and from 50° to 180° C., separating the discharge from the precarbonylation stage into an organic phase containing the main part of the rhodium and into an aqueous phase containing the complexing agent, and feeding the organic phase to the hydroformylation stage for the hydroformylation of the olefin in the presence of synthesis gas at from 50 to 1,000 bar and at from 60° to 180° C.

According to the invention, the rhodium-containing hydroformylation discharges obtained in the hydroformylation with bare rhodium are mixed with water-soluble, phosphorus-containing complexing agents, for example monodentate or polydentate complexing agents, which react with the rhodium catalyst to form complexes which are hydrophilic and, owing to their good water solubility, can, with water, extract the rhodium catalyst from the organic medium of the hydroformylation discharge. After the rhodium catalyst contained in the hydroformylation discharge has been extracted in the form of a water-soluble complex with the complexing agent used according to the invention, the hydroformylation product can be worked up in a conventional manner, for example by isolating it from the organic extract by distillation or by distilling off more readily volatile organic components of the hydroformylation discharge from more poorly volatile or even nondistillable hydroformylation products. The aqueous extract of the hydroformylation discharge which contains the rhodium now complexed by the phosphorus-containing complexing agent is passed to a processing stage in which the complexed rhodium is carbonylated in the presence of an essentially water-insoluble, organic liquid and in the presence of carbon monoxide or of a carbon monoxide-containing gas mixture at in general from 5 to 600, preferably from 10 to 400, particularly preferably from 20 to 300, bar and at from 50° to 150° C., preferably from 70° to 130° C., in particular from 80° to 110° C. As a result of the carbonylation, the rhodium is removed from the hydrophilic complex with the phosphorus-containing complexing agent, and the resulting, lipophilic rhodium carbonyl compound migrates into the water-insoluble, organic liquid. This step is referred to as precarbonylation since the carbonylation of the rhodium does not take place in the hydroformylation reactor itself but in fact in the precarbonylation stage upstream of said reactor. Instead of the abovementioned pressure, a higher pressure may also be used in the precarbonylation stage, without as a result adversely affecting the feasibility of the precarbonylation; for example, a pressure of from 5 to 1,000 bar may be employed, but the use of the abovementioned pressure ranges is particularly advantageous.

The discharge from the precarbonylation stage can be separated readily, for example in a phase separator, into an organic phase containing the main part of the rhodium in the form of a rhodium carbonyl compound and into an aqueous phase containing the complexing agent. The organic phase is then fed to the hydroformylation stage, in which the rhodium contained in the organic phase is converted into the bare rhodium catalyst which catalyses the hydroformylation of the olefin to be hydroformylated. The aqueous phase containing the complexing agent may be otherwise used, for example advantageously for the extraction of the rhodium catalyst from the hydroformylation discharge.

The use of such a precarbonylation stage leads to considerable advantages. Since the carbonylation takes place in general more rapidly and under milder conditions than the hydroformylation reaction, on the one hand the phosphorus-containing complexing agent can be subjected to less stringent reaction conditions for a shorter residence time and thus protected and, on the other hand, smaller reactor dimensions can be employed to obtain the same space-time yield, since the aqueous phase no longer enters the hydroformylation reactor. The expensive use of assistants, such as solubilizers, ultrasonics or highly concentrated aqueous solutions of the complex ligands, is likewise not required in the novel process.

The precarbonylation can be carried out with the aid of carbon monoxide, synthesis gas or a carbon monoxide-containing gas mixture.

For the purposes of this application, carbon monoxide-containing gas mixtures are understood as meaning carbon monoxide-containing gas mixtures which are not covered by the term synthesis gas, for example $CO/H_2$ mixtures having a composition which differs from that of synthesis gas, or mixtures of carbon monoxide with other gases which are inert under the reaction conditions, such as nitrogen, noble gases or lower hydrocarbons, such as methane, ethane, propane or butane. The content of inert gases in such carbon monoxide-containing gas mixtures is in general less than 60, preferably less than 50, in particular less than 30, % by volume. When such carbon monoxide gas mixtures containing inert gases are used, it may be necessary, depending on the composition of these gas mixtures, particularly in the case of a high inert gas content, to carry out the precarbonylation at a higher pressure and/or at a higher temperature than the pressures and temperatures defined as advantageous for carrying out the precarbonylation, in order to ensure a satisfactory conversion. The optimum conditions for this purpose can be determined in a simple preliminary experiment.

Preferably, however, the precarbonylation is carried out using carbon monoxide which, depending on the origin and for technical reasons, may contain less than 10, preferably less than 5, particularly less than 1, % by volume of inert gases or hydrogen.

According to the invention, a large number of liquids which are inert under the reaction conditions of the precarbonylation stage and of the hydroformylation stage may be used as essentially water-insoluble organic liquid, inert meaning that these liquids do not adversely affect the course of the precarbonylation or of the hydroformylation.

For example, hydrocarbons may be used as such organic liquids. Preferably, however, aldehydes or alcohols or mixtures of aldehydes and alcohols are used. For example, some of the crude discharge from the hydroformylation stage may be used for this purpose; however, it is also possible to use the aldehydes or alcohols formed in the hydroformylation stage and subsequently isolated, or mixtures thereof. There are virtually no restrictions with regard to the type of aldehydes used as water-insoluble, organic liquid in the precarbonylation stage. However, aldehydes or alcohols as formed in the hydroformylation of the olefin to be hydroformylated are preferably used.

High boilers may also be used as essentially water-insoluble, organic liquid in the precarbonylation stage. These are high-boiling condensates of aldehydes which are formed as byproducts in the course of the hydroformylation. They are of course generally multicomponent mixtures. The chemical nature of such mixtures of high boilers is described by way of example in U.S. Pat. No. 4,148,830. Such mixtures of high boilers are also commercially available, for example under the name Texanol® from Eastman.

In the novel process, olefins are particularly preferably used as essentially water-insoluble, organic liquid in the precarbonylation stage. Although there are in principle no restrictions with regard to the type of olefin used in the precarbonylation, olefins as used in the subsequent hydroformylation stage are preferably employed.

It may also prove advantageous to pass the entire olefin feed for the hydroformylation stage first through the precarbonylation stage. When carbon monoxide or carbon monoxide-containing gas mixtures are used as the carbonylating agent, acyl complexes of the carbonylated rhodium may form with the olefin, with the result that additional stabilization of the homogeneously dissolved rhodium can be achieved.

Surprisingly, it was found that, when α-olefins are used in the precarbonylation stage, isomerization of the α-olefins to internal olefins can occur. Thus, α-olefins can be isomerized according to the invention to give internal olefins and the latter hydroformylated in the subsequent hydroformylation stage to give internal, ie. branched, aldehydes. This is particularly advantageous since α-olefins are commercially available in larger amounts than internal olefins, α-olefins are also more economically obtainable than internal olefins and branched aldehydes and branched alcohols are desirable intermediates for the preparation of branched carboxylic acids, alcohols and amines, which in turn are used in large amounts, for example as additives for detergents and cleaning agents and for the preparation of biodegradable surfactants.

For the preparationof branched alcohols and/or aldehydes from α-olefins by the novel process, the α-olefin feed is advantageously passed through the precarbonylation stage. The precarbonylation and, simultaneously, the isomerization of the α-olefin to the internal olefin are generally carried out within the temperature and pressure ranges stated for the precarbonylation stage, a pressure of less than 100 bar and a temperature of more than 110° C. being advantageously established. The residence time of the α-olefin in the precarbonylation stage which is required for complete isomerization of the α-olefin is in general dependent on the reaction conditions used therein and is advantageously determined by a preliminary experiment.

Of course, the novel process can also be used for hydroformylating α-olefins to n-aldehydes, for example by passing the α-olefin into the hydroformylation reactor with bypassing of the precarbonylation stage, or by carrying out the precarbonylation at more than 100 bar and at below 110° C.

The precarbonylation stage may consist of one or more reactors connected in parallel or in series. For this purpose, a batchwise procedure may be carried out using conventional stirred autoclaves, and a continuous procedure using cascades of stirred autoclaves or tube reactors which contain suitable apparatuses, such as stirrers or static mixers, for thorough mixing of the reaction mixture.

The discharge from the precarbonylation stage is separated in a suitable apparatus, for example a phase separator, into an aqueous and an organic phase. The phase separation can be carried out under superatmospheric pressure, for example under the operating pressure of the precarbonylation stage, or at atmospheric pressure after the pressure of the discharge from the precarbonylation stage has been let down beforehand. Since both the precarbonylation and the hydroformylation are carried out under superatmospheric pressure, the phase separation is advantageously also carried out under pressure.

The organic phase which is thus separated from the discharge of the precarbonylation stage and contains the rhodium required for catalysing the hydroformylation and, depending on the type of water-insoluble, organic liquid used in the precarbonylation stage, the olefin to be hydroformylated and another suitable organic liquid is fed to the hydroformylation stage. If the precarbonylation discharge was not let down and degassed, the organic phase still contains the gaseous carbonylating agent used in the precarbonylation stage, some of it being present in dissolved form.

The hydroformylation is carried out in the presence of synthesis gas with the aid of the carbonylated rhodium produced in the precarbonylation stage. Synthesis gas is generally understood as meaning carbon monoxide/hydrogen gas mixtures having a hydrogen content of from 10 to 90, in particular from 40 to 60, % by volume. If necessary, the olefin to be hydroformylated is also fed to the hydroformylation stage unless it was already fed to the hydroformylation stage together with the organic phase from the precarbonylation discharge.

The hydroformylation is carried out in general at from 60° to 180° C., preferably from 80° to 150° C., particularly preferably from 90° to 130° C., and at in general from 50 to 1,000, preferably from 70 to 500, in particular from 100 to 400, bar. Otherwise, the hydroformylation is effected under conditions as usually used in hydroformylations with bare rhodium and as described, for example, in the literature cited at the outset and relating to hydroformylation with bare rhodium.

The product ratio alcohol/aldehyde in the hydroformylation discharge may be influenced depending on the pressure and temperature conditions used in the hydroformylation stage and on the composition of the synthesis gas. For example, a molar aldehyde/alcohol ratio of 93:7 is obtained in each case in the hydroformylation of trimeric propylene with the same compositions of the synthesis gas in each case—molar $CO/H_2$ ratio of 50:50, 40:60 or 60:40—at 130° C. and 280 bar. When the temperature is increased from 130° C. to 150° C., the molar aldehyde/alcohol ratio in the hydroformylation discharge changes depending on the composition of the synthesis gas—molar $CO/H_2$ ratio 50:50, 40:60 and 60:40 to 76:24, 67:33 and 82:18, respectively.

The hydroformylation can be carried out in the presence or absence of organic solvents. The use of organic solvents is particularly advantageous, for example in the hydroformylation of long-chain or polymeric olefins. Suitable solvents are the solvents usually used in the hydroformylation process, for example high-boiling aromatic and aliphatic hydrocarbons or high-boiling aldehyde condensates which are formed as byproducts in the course of the hydroformylation reaction as a result of the condensation of the aldehyde products.

The discharge from the hydroformylation stage is advantageously let down before being extracted with the aqueous solution of the phosphorus-containing complexing agent. The extraction of the hydroformylation discharge is carried out in general at from 80° to 140° C., preferably from 90° to 130° C., in particular from 100° to 120° C., and at in general from 1 to 20, preferably from 1 to 10, particularly from 1 to 5, bar. The extraction can be carried out in the air or under an inert gas atmosphere, for example a nitrogen, hydrogen or argon atmosphere; however, it may also be advantageous additionally to mix carbon monoxide or synthesis gas with the inert gas used or to carry out the extraction in the presence of carbon monoxide.

A fresh aqueous solution of the complexing agent can be used for extracting the rhodium catalyst from the hydroformylation discharge; however, the aqueous phase which is obtained in the phase separation of the precarbonylation discharge and contains the dissolved complexing agent is preferably used for this purpose, said aqueous phase being recycled for this purpose to the extraction stage.

In the extraction, a volume ratio of aqueous to organic phase of in general from 0.2:1 to 2:1, preferably from 0.3:1 to 1:1, is generally established. The molar ratio of phosphorus-containing complexing agent to rhodium in the extraction is in general from 5:1 to 10,000:1, preferably from 10:1 to 5,000:1, in particular from 50:1 to 1,000:1.

Virtually all liquid-liquid extraction apparatuses are suitable for extracting the hydroformylation discharge with the aqueous solution of the complexing agent, for example mixer-settler apparatuses, bubble columns or countercurrent or cocurrent extraction columns, and these may also be provided with additional baffles for better mixing of aqueous and organic phase, for example with sieve trays, packings or static mixers. The extraction of the rhodium catalyst from the hydroformylation discharge can be carried out in one stage; a multistage extraction is preferably used, for example a two- or three-stage extraction, and the aqueous phase containing the complexing agent can be fed cocurrent or, particularly preferably, countercurrent with respect to the organic phase.

After the end of the extraction, the hydroformylation discharge freed from the rhodium catalyst can be worked up in a conventional manner, for example by distillation, in order to isolate the desired alcohol and/or aldehyde products contained therein.

An advantageous embodiment of the novel process is shown schematically in the FIGURE and is described below. Self-evident details of the apparatus which are not required for illustrating the novel process have been omitted from the FIGURE for reasons of clarity. The embodiment of the novel process shown in the FIGURE comprises the process stages of hydroformylation, a two-stage countercurrent extraction of the hydroformylation discharge by means of mixer-settler apparatuses and the precarbonylation stage. Of course, other extraction apparatuses of the above-mentioned types may also be used instead of the mixer-settler apparatuses.

In the embodiment of the novel process according to the FIGURE, the hydroformylation discharge from the hydroformylation reactor 1 is let down and, if required, mixed with inert gas (not shown) and then introduced via line 2 into the extraction stage A, comprising the mixer-settler apparatus 3/4, where it is extracted with the aqueous solution of the phosphorus-containing complexing agent from extraction stage C (mixer-settler apparatus 6/7), which solution is fed in via line 19. When the plant is started up or for supplementing the complexing agent solution, fresh complexing agent solution can be fed via an inlet which is not shown in the FIGURE, for example to the mixer 3. The extraction mixture contained in the mixer 3 is separated in the settler 4 into a first organic phase and a first aqueous phase. The first aqueous phase is passed via line 8 into the precarbonylation reactor, whereas the first organic phase is fed via line 5 to the extraction stage C. Before being introduced into the precarbonylation reactor 11, the first aqueous phase is mixed via the feeds 9 and 10 with an essentially water-insoluble, organic liquid, for example crude hydroformylation discharge, Texanol® or preferably the olefin to be hydroformylated, and the carbonylating agent, ie. carbon monoxide or a suitable carbon monoxide-containing gas mixture, preferably mixed with carbon monoxide. It is in principle also possible for the starting materials fed in via the lines 9 and 10 to be passed directly into the precarbonylation reactor 11. In the precarbonylation reactor 11, the rhodium bonded to the phosphorus-containing complexing agent and present in the aqueous phase is carbonylated under the stated conditions, and the resulting, lipophilic rhodium carbonyl compound migrates into the organic phase. The discharge from the precarbonylation reactor 11 is passed via line 12, preferably without being let down beforehand, into the phase separator 13 and is separated there into a second organic phase and a second aqueous phase (phase separation B).

The second organic phase, which, in addition to the water-insoluble, organic liquid, also contains the rhodium required for catalysing the hydroformylation and may contain excess carbonylating agent, is passed via line 14 into the hydroformylation reactor 1. Synthesis gas is passed via line 15 to the hydroformylation reactor, but alternatively may also be passed directly into hydroformylation reactor 1. If an olefin was not used as the water-insoluble, organic liquid in the precarbonylation reactor, the olefin to be hydroformylated can either be passed directly via line 16 into the hydroformylation reactor 1 or mixed beforehand, via an inlet not shown in the FIGURE, with the stream in line 14. In the hydroformylation reactor, the olefin is hydroformylated under the stated conditions to give the corresponding alcohols and/or aldehydes.

The second aqueous phase from phase separation B, which contains the solution of the phosphorus-containing complexing agent which has a low concentration of rhodium, is fed via line 17, if necessary after being let down beforehand, to the mixer 6. In the extraction stage C, comprising the mixer 6 and the settler 7, the first organic phase from extraction stage A is extracted again with the second aqueous phase from phase separation B in order to remove residual amount of rhodium from the first organic phase. The extraction mixture contained in the mixer 6 is separated in the settler 7 into a third organic phase and a third aqueous phase. The third organic phase now freed from rhodium is discharged via line 18 for further working up to isolate the desired products—alcohol and/or aldehyde. The third aqueous phase from extraction C is passed via line 19 into the extraction stage A, with which the circulation is complete.

The initial filling of the reactor with rhodium can be effected by introducing a solution or suspension of the rhodium catalyst or one of the precursor compounds suitable for the preparation of the rhodium catalyst and mentioned at the outset, for example into the precarbonylation reactor 11 or into the hydroformylation reactor 1. The same applies to any necessary replenishment of spent catalyst. It is also possible to introduce the rhodium into the plant via line 20 or other inlets not shown in the FIGURE, for example via an inlet in line 8.

Sulfonated, phosphorus-containing complexing agents selected from the group consisting of the mono- or polysulfonated mono- or oligophosphines or the mono- or polysulfonated mono- or oligophosphites and/or from the group consisting of the mono- or polycarboxylated mono- or oligophosphines or the mono- or polycarboxylated mono- or oligophosphites are preferably chosen as complexing agents which form water-soluble complexes with the rhodium catalyst dissolved in the discharge from the hydroformylation reaction.

Under the action of these complexing agents, coordinate bonds with a central rhodium atom of the rhodium catalyst presumably form via the free electron pair of the phosphorus atoms, some of the carbon monoxide bonded to the central rhodium atom of the rhodium catalyst presumably being reversibly displaced by these ligands under the conditions of complex formation. The presence of sulfo or carboxyl groups in the phosphorus-containing complexing agents used according to the invention is critical for the feasibility of the novel process. The complexing agents may contain one or more carboxyl and/or sulfo groups per molecule, the number of carboxyl and/or sulfo groups in the molecule also being dependent, of course, on the molecular size of the complexing agent and its reactivity with respect to sulfonating reagents. The number of carboxyl and/or sulfo groups in the molecule of the complexing agent influences the water solubility of this complexing agent. Of course, phosphorus-containing complexing agents which contain both carboxyl groups and sulfo groups as substituents or mixtures of sulfonated and carboxyl-containing complexing agents may also be used in the novel process. In the complexing agents used according to the invention, the sulfo and carboxyl groups are preferably present in salt form, in particular in the form of water-soluble salts, particularly preferably in the form of their onium, alkali metal and/or alkaline earth metal salts. For example, water-soluble ammonium, phosphonium or arsonium salts of the relevant carboxylic or sulfonic acids may be used. To avoid misunderstandings, it is expressly pointed out here that the phosphorus-containing complexing agent sulfonates or carboxylates which can be used according to the invention carry the sulfo or carboxyl groups as substituents and are not bonded, for example, in salt-like form with any sulfonate or carboxylate anions.

Sulfonated arylphosphines, in particular sulfonated triarylphosphines, sulfonated triaralkylphosphines or alicyclic, sulfonated aryl-containing phosphines are preferably used in the novel process. The use of sulfonated aryl phosphites, in particular sulfonated triaryl phosphites, is also preferred. These aryl-containing complexing agents can be particularly simply prepared by conventional methods, for example by sulfonation of the corresponding phosphines or organophosphites by means of concentrated sulfuric acid or sulfuric acid/sulfo trioxide mixtures, which are also referred to as oleum, or by means of chlorosulfonic acid.

In the sulfonation of these phosphines or organophosphites by the abovementioned method, mixtures of mono- or polysulfonated products may form depending on the phosphine or phosphite used as starting material. These sulfonation products consisting of various sulfonated compounds can of course be separated into the individual, sulfonated components by prior art methods, such as crystallization or ion exchange chromatography, and the individual components thus obtained can be used as complexing agents in the novel process. However, since the sulfonated individual compounds generally do not have substantially better properties as complexing agents than the product mixture from the sulfonation, the sulfonated product mixture is advantageously used as the complexing agent, dispensing with the separation of the mixture into its individual components.

Examples of water-soluble, sulfonated phosphines which may be used as complexing agents in the novel process are: diphenylphosphinephenyl-m-sulfonic acid, phenylphosphinedi(m-phenylsulfonic acid), triphenylphosphinetri(m-sulfonic acid) (for preparation, cf. DE-A 32 35 030; DE-A 34 31 643; Schindlbauer: Monatsh. Chem. 96, (1965) 2051, W. A. Herrmann et al: Angew. Chem. 105, (1993) 1588, W. A. Herrmann et al: J. Organomet. Chem. 339, (1990) 85, sulfonated tris(ω-phenylalkyl) phosphines (preparation: Bartik et al: Organometallics 12, (1993) 164), sulfonated 2,2'-bis(di-phenylphosphinomethyl) biphenyls, as described, together with their preparation, in EP-A 4 912 40 and by W. A. Herrmann et al: J. Mol. Cat. 73, (1992) 191, and 3,4-dimethyl-2,5,6-tris(m-sulfonatophenyl)-1-phosphanorbornadiene (DE-A 42 20 267). Further sulfonated, water-soluble phosphines suitable as complexing agents are disclosed, for example, in W. A. Herrmann et al., Angew. Chem. 105, (1993) 1588, Barton et al., J. Coord. Chem. 24, (1991) 43, and Kalck et al., Adv. Organomet. Chem. 34, (1992) 219. Other preparation methods for water-soluble, sulfonated phosphines are described by Sinou, Bull. Soc. Chim. France (1987) 480. The abovementioned citations are incorporated as references in this application with respect to the sulfonated, water-soluble phosphines described therein. In addition to the sulfo group, the aryl groups of these sulfonated phosphines may also carry 1 or 2 substituents which are inert under the reaction conditions, for example $C_1$–$C_4$-alkyl, $C_1$–$C_4$-alkoxy, halogen, in particular fluorine, chlorine or bromine, hydroxyl, nitro, carboxyl or nitrile. However, the unsubstituted, sulfonated phosphines are preferably used. These sulfonated phosphines are particularly advantageously used in the form of their water-soluble salts with alkali metals or alkaline earth metals, preferably with alkali metals, in particular in the form of their lithium, sodium or potassium salts. They may also be used in the form of their water-soluble ammonium salts.

For example, carboxylated phosphines whose carbon skeleton corresponds to the abovementioned sulfonated triarylphosphines but carries 1 to 3 carboxyl groups instead of the sulfo groups can be used as such. These carboxylated triarylphosphines can be prepared, for example, by the processes described by Gilman et al., J. Am. Chem. Soc. 67, (1945) 824, Luckenbach et al., Z. Naturforsch B, 32, (1977) 1038, or Schumann et al., Synth. Comm. 22, (1992) 841.

Other water-soluble, carboxylated phosphine ligands suitable for the novel process are ligands of the general formula I

$$Ar_{3-n}P(CH_2COOH)_n \quad\quad\quad I$$

where Ar is an unsubstituted or substituted phenyl ring, preferably a phenyl ring which is unsubstituted or substituted by a carboxyl group, and n is an integer from 1 to 3, and ligands of the general formula II

$$\underset{HOOCH_2C-P-CH_2-CH_2-P-CH_2COOH}{\overset{R^1 \quad\quad\quad\quad R^2}{|\quad\quad\quad\quad\quad|}} \quad\quad II$$

where $R^1$ and $R^2$ are identical or different and are each an unsubstituted or substituted phenyl ring, preferably a phenyl ring which is unsubstituted or substituted by a carboxyl group, or are each a —$CH_2$—COOH group, and ligands of the general formula III

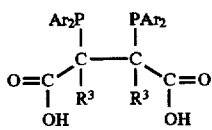

where Ar is an unsubstituted or substituted phenyl ring, preferably a phenyl ring which is unsubstituted or substituted by a carboxyl group, and the radicals $R^3$ are identical and are each hydrogen or together form a chemical bond.

Examples of compounds of the general formula I, II and III are diphenylphosphinopropionic acid (preparation: Mann et al., J. Chem. Soc. (1957) 4453), P,P'-diphenylethylenediphosphino-P,P'-diacetic acid of the formula

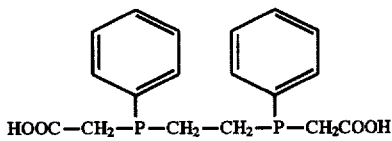

which can be prepared according to Podlahava et al., J. Inorg. Nucl. Chem. 40, (1978) 967, ethylendiphosphino-P, P,P',P'-tetraacetic acid of the formula

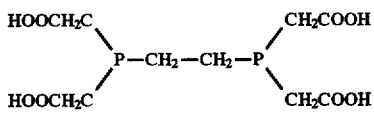

which can be prepared according to Podlahava et al., Coll. Czech. Chem. Comm. 45, (1980) 2049, 2,3-bis(diphenylphosphino)maleic acid of the formula

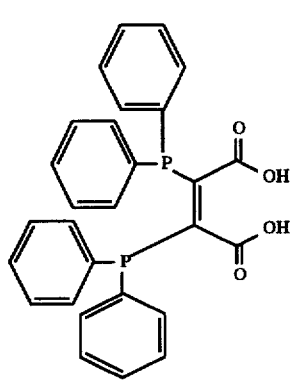

which can be prepared according to Avey et al., Inorg. Chem. 32, (1993) 233, and the 2,3-bis(diphenylphosphino)succinic acid obtainable therefrom by hydrogenation of the double bond.

The carboxylated phosphine ligands are used in the novel process preferably in the form of their water-soluble salts, in particular in the form of their water-soluble alkali metal salts, preferably in the form of their lithium, sodium or potassium salts, or in the form of their water-soluble ammonium salts. Instead of sulfonated or carboxylated water-soluble phosphines, or as a mixture with these, it is also possible to use water-soluble, sulfonated organophosphites as complexing agents in the novel process. Since these organophosphites are used in an aqueous medium, they must have sufficient stability to hydrolysis. Such sulfonated organophosphites which are stable to hydrolysis and their preparation are described, for example, in Fell et al., J. Prakt. Chem. 335, (1993) 75, which is herewith incorporated by reference. Instead of the lipophilic ammonium salts of sulfonated phosphite ligands, described by Fell et al., their water-soluble alkali metal salts are used in the novel process.

Complexing agents which are particularly preferably used in the novel process are triphenyltri(m-sulfonic acid) and the water-soluble, sulfonated derivatives of 2,2'-bis-(diphenylphosphinomethyl)-biphenyl and their water-soluble salts, in particular their alkali metal salts, preferably their lithium, sodium or potassium salts. Water-soluble, sulfonated derivatives of 2,2'-bis-(diphenylphosphinomethyl)-biphenyl IV

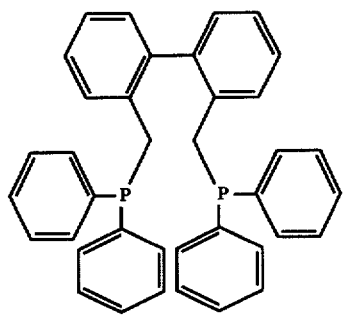

are understood as meaning the mixtures of the tetra-, penta- and hexasulfonated compounds IV, which mixtures are obtained in the sulfonation of IV by means of sulfuric acid/sulfur trioxide mixtures (cf. J. Mol. Cat. 73, (1992) 191). These mixtures can be used in the novel process without further separation into their individual components having different degrees of sulfonation. As stated above, these mixtures of the sulfonated derivatives of IV are preferably used in the form of their water-soluble alkali metal salts.

As is evident from the above statements, a large number of sulfonated or carboxylated phosphines or, provided that they are stable to hydrolysis, sulfonated or carboxylated organophosphites can be used as complexing agents in the novel process. In this context, it should be noted that, with the use of these complexing agents, all that is important is their ability to form, with the bare rhodium dissolved in the organic phase of the hydroformylation discharge, water-soluble complexes which on the one hand are sufficiently stable to stabilize the extracted rhodium in the aqueous phase and on the other hand liberate the complexed rhodium again under the conditions of the precarbonylation stage so that, after carbonylation of the rhodium, the latter can migrate back into the organic phase. The properties of some of the stated complexing agents with respect to modifying the hydroformylation properties are irrelevant for their use as complexing agents in the novel process since bare rhodium serves as a hydroformylation catalyst in the novel process and not as a complex of rhodium with one of the abovementioned ligands.

The novel process is particularly suitable for the hydroformylation of olefins of more than 3, preferably more than 7, carbon atoms, in particular for the hydroformylation of $C_7$–$C_{20}$-olefins which may be straight-chain or branched and may contain α-olefinic and/or internal double bonds, eg. 1-octene, 1-dodecene, trimeric and tetrameric propylene or dimeric, trimeric and tetrameric butylene. Unsaturated oligomers of other olefins may also be hydroformylated, as may cooligomers of different olefins.

The aldehydes formed from these olefins are used, for example, as intermediates for the preparation of plasticizer alcohols and surfactants, which can be produced therefrom in a conventional manner by hydrogenation. The olefins used for the hydroformylation can be obtained, for example, by the acid-catalyzed elimination of water from the corresponding fatty alcohols or by many other industrial processes, as described, for example, in Weissermel, Arpe: Industrielle Organische Chemie, pages 67–86, Verlag Chemie, Weinheim, 1978. If α-olefins are used in the novel process, they may alternatively be hydroformylated to the corresponding n-aldehydes by direct introduction into the hydroformylation stage or hydroformylated as a result of being introduced into the precarbonylation stage, after their isomerization to internal olefins, to give isoaldehydes, the use of which has already been referred to.

The novel process is also particularly suitable for the hydroformylation of polymeric olefins, for example low molecular weight polyisobutene, low molecular weight polybutadiene or low molecular weight 1,3-butadiene/isobutene or butene copolymers. Low molecular weight polymers are understood as meaning in particular polymers having molecular weights of from 500 to 5,000 Dalton. However, higher molecular weight, unsaturated polymers may also be hydroformylated. The only precondition for this is that they are soluble in the hydroformylation medium. The hydroformylation products of these polymeric olefins, in particular those of low molecular weight polyisobutene, can be converted by reductive amination, for example by the process of EP-A 244 616, into the corresponding amines, which are used as fuel additives. Low molecular weight polyisobutene is obtainable, for example, by the process of EP-A 145 235, a low molecular weight isobutene/1,3-butadiene copolymers can be obtained, for example, by the process of DE-A 43 06 384.

The novel process is suitable in practice for the preparation of all aldehydes which are obtainable by the hydroformylation of olefins. It should be pointed out in particular that, for example, substituted olefins which in general may carry 1 or 2 substituents, preferably one substituent, can also be hydroformylated by the novel process. For example, unsaturated, aliphatic carboxylates, acetals, alcohols, ethers, aldehydes, ketones and amines and amides can be hydroformylated by the novel process. For example, methacrylates, dicyclopentadiene, vinyl and allyl ethers, in particular corresponding derivatives of unsaturated fatty acids, for example the esters of oleic, linoleic, linolenic, ricinoleic and erucic acid, are of interest as such substituted starting olefins. The aldehydes obtainable from these olefinic raw materials by hydroformylation are also starting materials for the preparation of readily biodegradable, detergent substances.

A further embodiment of the present invention relates to processes for the preparation of branched carboxylic acids, alcohols or amines from α-olefins, the α-olefins being isomerized to internal olefins in the precarbonylation stage of the novel process and then being hydroformylated to isoaldehydes, and the isoaldehydes thus obtained being oxidized in a conventional manner to branched carboxylic acids, reduced to branched alcohols or reductively aminated to branched amines.

The oxidation of the isoaldehydes or isoaldehyde/n-aldehyde mixtures obtained according to the invention from α-olefins can be carried out in a conventional manner, for example by oxidation of the aldehydes with atmospheric oxygen or oxygen according to the processes as described, for example, in Ullmann's Encyclopedia of Industrial Chemistry, 5th edition, Vol. A5, page 239, VCH Verlagsgesellschaft, Weinheim, 1986.

The catalytic hydrogenation of the isoaldehydes or isoaldehyde/n-aldehyde mixtures obtainable by the novel process from α-olefins to branched alcohols can be effected in a manner known per se, for example by the processes described in Ullmann's Encyclopedia of Industrial Chemistry, 5th edition, Vol. A1, page 279, VCH Verlagsgesellschaft, Weinheim, 1985, or G. H. Ludwig, Hydrocarbon Processing, March 1993, page 67.

The reductive amination of the isoaldehydes or isoaldehyde/n-aldehyde mixtures obtainable by the novel process from α-olefins can be carried out in a manner known per se, for example by the process described in Ullmann's Encyclopedia of Industrial Chemistry, 5th edition, Vol. A2, page 1, VCH Verlagsgesellschaft, Weinheim, 1985. Ammonia, primary $C_1$–$C_{20}$-amines or secondary $C_2$–$C_{20}$-amines may be used as starting material for the preparation of amines.

EXAMPLE

The discharge from the hydroformylation of octene-N—an isomer mixture of butene dimers—was extracted into water using a 2% strength by weight solution of tris-(sodium-m-sulfonatophenyl)phophine (TPPTS). The aqueous solution was enriched with 80 ppm by weight of rhodium. 75 ml of this solution was stirred with octene-N in an autoclave at a carbon monoxide pressure of 280 bar and at 130° C. for 3 hours. During this procedure, the rhodium bonded to the complexing agent TPPTS was carbonylated and liberated from the water-soluble complexing agent. Samples of the aqueous and organic phases were taken from the autoclave under pressure. The organic phase contained 84 ppm by weight of rhodium, and the aqueous phase 3 ppm by weight. The TPPTS complexing agent had remained in the aqueous phase.

The discharge from the precarbonylation reactor was separated under pressure into an aqueous phase and an organic phase. The organic phase was then hydroformylated in a hydroformylation reactor at 130° C. and a synthesis gas pressure ($CO/H_2$ ratio 1:1) of 280 bar. The conversion in the hydroformylation was 93%.

We claim:

1. A process for the preparation of aldehydes or aldehydes and alcohols by the hydroformylation of olefins of more than 3 carbon atoms, comprising the stage of hydroformylation by means of an unmodified rhodium catalyst homogeneously dissolved in the reaction medium, the separation of the rhodium catalyst from the discharge of the hydroformylation reaction and the recycling of the rhodium separated from the hydroformylation discharge into the hydroformylation stage, wherein the separation of the rhodium catalyst is achieved by extraction from the hydroformylation discharge into the aqueous phase by means of an aqueous solution of a water-soluble, phosphorus-containing complexing agent selected from the group consisting of the mono- or polysulfonated mono- and oligophosphines or the mono- or polysulfonated oligophosphites and/or from the group consisting of the mono- or polycarboxylated mono- or oligophosphines, and the aldehyde or the aldehyde and the alcohol is or are isolated from the extracted hydroformylation discharge, the aqueous rhodium-containing extract is fed to a precarbonylation stage and is subjected to a precarbonylation in the precarbonylation stage in the presence of an essentially water-insoluble organic liquid and in the presence of carbon monoxide or of a carbon monoxide-containing gas mixture at from 5 to 600 bar and from 50° to 180° C., the discharge from the precarbonylation stage is separated into an organic phase containing the main part of the rhodium and into an aqueous phase containing the complexing agent, and the organic phase is fed to the hydroformylation stage for hydroformylation of the olefin in the presence of synthesis gas at from 50 to 1,000 bar and at from 60° to 180° C.

2. A process as claimed in claim 1, wherein the extraction of the rhodium catalyst from the hydroformylation discharge is carried out at from 80° to 140° C. and at from 1 to 20 bar.

3. A process as claimed in claim 1, wherein the extraction of the rhodium catalyst is carried out in one or more stages and the aqueous solution of the complexing agent is fed countercurrent to the hydroformylation discharge in the extraction.

4. A process as claimed in claim 1, wherein the aqueous phase obtained after removal of the organic phase containing the main part of the rhodium after the precarbonylation stage and containing the complexing agent is used for extracting the rhodium catalyst from the hydroformylation discharge.

5. A process as claimed in claim 1, wherein the process is carried out continuously in a plant comprising a precarbonylation unit, a hydroformylation unit and a one-stage or multistage extraction unit.

6. A process as claimed in claim 1, wherein linear or branched α-olefins or internal olefins which are unsubstituted or substituted by 1 or 2 substituents which are inert under the reaction conditions, or mixtures of these olefins, are hydroformylated in the presence or absence of a solvent.

7. A process as claimed in claim 1, wherein propene or butene oligomers or cooligomers are hydroformylated.

8. A process as claimed in claim 1, wherein low molecular weight polyisobutenes, polybutadienes or isobutene/1,3-butadiene copolymers are hydroformylated.

9. A process as claimed in claim 1, wherein unsaturated fatty acid derivatives are hydroformylated.

10. A process as claimed in claim 1, wherein the discharge from the hydroformylation stage is extracted in an extraction stage A with the aqueous solution of the phosphorus-containing complexing agent from extraction stage C, this extraction mixture is separated into a first aqueous phase and a first organic phase, the first aqueous phase is fed to the precarbonylation stage and the first organic phase is fed to extraction stage C, in the precarbonylation stage, the complexed rhodium contained in the first aqueous phase is carbonylated in this carbon monoxide, synthesis gas or a carbon monoxide-containing gas mixture in the presence of an essentially water-insoluble, organic liquid, the discharge from the precarbonylation stage is separated in a phase separation B into a second organic phase and a second aqueous phase, the second organic phase containing the carbonylated rhodium is fed to the hydroformylation reactor and the second aqueous phase containing the complexing agent is fed to extraction stage C, in the hydroformylation stage, the olefin is hydroformylated in the presence of synthesis gas, the second aqueous phase is used for extracting residual rhodium catalyst from the first organic phase in extraction stage C, the extraction mixture from extraction stage C is separated into a third organic phase and a third aqueous phase, the aldehyde or the alcohol is isolated from the third organic phase, and the third aqueous phase is recycled to extraction stage A for extracting the rhodium catalyst from the hydroformylation discharge.

11. A process as claimed in claim 1, wherein some of the crude discharge from the hydroformylation stage is used in the precarbonylation stage as essentially water-insoluble, organic liquid.

12. A process as claimed in claim 1, wherein an aldehyde or alcohol is used in the precarbonylation stage as essentially water-insoluble, organic liquid.

13. A process as claimed in claim 12, wherein the aldehyde or alcohol formed in the hydroformylation stage is used after purification thereof or a purified mixture of this aldehyde and alcohol is used.

14. A process as claimed in claim 1, wherein a mixture of high-boiling condensates of aldehydes is used in the precarbonylation stage as essentially water-insoluble, organic liquid.

15. A process as claimed in claim 1, wherein an olefin is used in the precarbonylation stage as essentially water-insoluble, organic liquid.

16. A process as claimed in claim 1, wherein the α-olefin to be hydroformylated is used in the precarbonylation stage as essentially water-insoluble liquid and the precarbonylation is carried out at more than 100 bar and at below 110° C.

17. A process as claimed in claim 1, wherein an α-olefin is used in the precarbonylation stage as essentially water-insoluble organic liquid and the precarbonylation is carried out at less than 100 bar and at above 110° C.

18. A process as claimed in claim 1, wherein a water-insoluble salt of mono-, di- or trisulfonated triphenylphosphine is used as the phosphorus-containing complexing agent.

19. A process as claimed in claim 1, wherein a water-soluble salt of tris (m-sulfonatophenyl) phosphine is used as the phosphorus-containing complexing agent.

20. A process as claimed in claim 1, wherein a sulfo-carrying water-soluble salt of 2,2'-bis (diphenylphosphinomethyl)-1,1'-biphenyl is used as phosphorus-containing complexing agent.

21. A process for the preparation of carboxylic acids from an internal olefin or an α-olefin, wherein the olefin is hydroformylated as claimed in claim 1 and the aldehyde formed is subsequently oxidized to the carboxylic acid in a manner known per se.

22. A process for the preparation of alcohols from an internal olefin or an α-olefin, wherein the olefin is hydroformylated as claimed in claim 1 and the aldehyde formed is subsequently reduced or hydrogenated to the alcohol in a manner known per se.

23. A process for the preparation of amines from an internal olefin or an α-olefin, wherein the olefin is hydroformylated as claimed in claim 1 and the aldehyde or alcohol formed is aminated with ammonia or a primary or secondary amine in the presence of an amination catalyst and hydrogen in a manner known per se.

* * * * *